(12) United States Patent
Spinelli et al.

(10) Patent No.: US 8,639,334 B2
(45) Date of Patent: Jan. 28, 2014

(54) METHODS AND APPARATUS FOR PREDICTING ACUTE RESPONSE TO CARDIAC RESYNCRONIZATION THERAPY AT A GIVEN STIMULATION SITE

(75) Inventors: Julio Spinelli, Shoreview, MN (US); Yinghong Yu, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1680 days.

(21) Appl. No.: 11/562,681

(22) Filed: Nov. 22, 2006

(65) Prior Publication Data

US 2007/0088401 A1 Apr. 19, 2007

Related U.S. Application Data

(63) Continuation of application No. 10/327,267, filed on Dec. 20, 2002, now Pat. No. 7,142,922.

(51) Int. Cl.
*A61B 5/04* (2006.01)
(52) U.S. Cl.
USPC .................................. 607/27; 607/25; 607/28
(58) Field of Classification Search
USPC ............................................... 607/17, 25, 28
See application file for complete search history.

(56) References Cited

U.S. PATENT DOCUMENTS

| 6,453,192 | B1 | 9/2002 | Ding et al. |
| 2002/0091333 | A1 | 7/2002 | Hsu et al. |
| 2002/0143264 | A1 | 10/2002 | Ding et al. |
| 2005/0216065 | A1 | 9/2005 | Ding et al. |

OTHER PUBLICATIONS

*Journal of the American College of Cardiology*, vol. 39. (2002),2026-2033.
"(PACE) Pacing and Clinical Electrophysiology", vol. 24, No. 4, Part II, (Apr. 2001),548.

*Primary Examiner* — Tammie K Heller
(74) *Attorney, Agent, or Firm* — Schwegman Lundberg & Woessner, P.A.

(57) ABSTRACT

Response to cardiac resynchronization therapy is predicted for a given stimulation site so that an atrioventricular delay of an implantable device administering cardiac resynchronization therapy may be set to a proper amount. The first deflection of ventricular depolarization is measured, such as through a surface electrocardiogram or through an intracardiac electrogram measured by a lead positioned in the heart at the stimulation site. The maximum deflection of the ventricular depolarization is then measured by the lead positioned at the stimulation site. The interval of time between the first deflection and the maximum deflection of the ventricular depolarization is compared to a threshold to determine whether the stimulation site is a responder site. If the interval is larger than the threshold, then the site is a responder and the atrioventricular delay of the implantable device may be set to less than the intrinsic atrioventricular delay of the patient. Otherwise, the atrioventricular may be set to approximately equal the intrinsic atrioventricular delay.

8 Claims, 10 Drawing Sheets

METHODS AND APPARATUS FOR PREDICTING ACUTE RESPONSE TO CARDIAC RESYNCRONIZATION THERAPY AT A GIVEN STIMULATION SITE

CROSS REFERENCE TO RELATED APPLICATION(S)

This application is a continuation of U.S. patent application Ser. No. 10/327,267, filed on Dec. 20, 2002, now U.S. Pat. No. 7,142,922, the specification of which is incorporated herein by reference.

TECHNICAL FIELD

The present invention relates generally to a method and apparatus for administering stimulation therapy for heart disease and, more particularly, to a method and apparatus for predicting acute response to cardiac resynchronization therapy for a given stimulation site.

BACKGROUND

The heart is a muscular organ comprising multiple chambers that operate in concert to circulate blood throughout the body's circulatory system. As shown in FIG. 1, the heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112. Oxygen-depleted blood returning to the heart 100 from the body collects in the right atrium 106. When the right atrium 106 fills, the oxygen-depleted blood passes into the right ventricle 108 where it can be pumped to the lungs (not shown) via the pulmonary arteries 117. Within the lungs, waste products (e.g., carbon dioxide) are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. When the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase (e.g., systole), the ventricular muscle cells of the right and left ventricles 108, 112 contract to pump blood through the pulmonary circulation and throughout the body, respectively. Conversely, during the diastolic phase (e.g., diastole), the ventricular muscle cells of the right and left ventricles 108, 112 relax, during which the right and left atriums 106, 110 contract to force blood into the right and left ventricles 108, 112, respectively. Typically, the cardiac cycle occurs at a frequency between 60 and 100 cycles per minute and can vary depending on physical exertion and/or emotional stimuli, such as, pain or anger.

The contractions of the muscular walls of each chamber of the heart 100 are controlled by a complex conduction system that propagates electrical signals to the heart muscle tissue to effectuate the atrial and ventricular contractions necessary to circulate the blood. As shown in FIG. 2, the complex conduction system includes an atrial node 120 (e.g., the sinoatrial node) and a ventricular node 122 (e.g., the atrioventricular node). The sinoatrial node 120 initiates an electrical impulse that spreads through the muscle tissues of the right and left atriums 106, 110 and the atrioventricular node 122. As a result, the right and left atriums 106, 110 contract to pump blood into the right and left ventricles 108, 112 as discussed above. At the atrioventricular node 122, the electrical signal is momentarily delayed before propagating through the right and left ventricles 108, 112. Within the right and left ventricles 108, 112, the conduction system includes right and left bundle branches 126, 128 that extend from the atrioventricular node 122 via the Bundle of His 124. The electrical impulse spreads through the muscle tissues of the right and left ventricles 108, 112 via the right and left bundle branches 126, 128, respectively. As a result, the right and left ventricles 108, 112 contract to pump blood throughout the body as discussed above.

Normally, the muscular walls of each chamber of the heart 100 contract synchronously in a precise sequence to efficiently circulate the blood as described above. In particular, both the right and left atriums 106, 110 contract (e.g., atrial contractions) and relax synchronously. Shortly after the atrial contractions, both the right and left ventricles 108, 112 contract (e.g., ventricular contractions) and relax synchronously. Several disorders or arrhythmias of the heart can prevent the heart from operating normally, such as, blockage of the conduction system, heart disease (e.g., coronary artery disease), abnormal heart valve function, or heart failure.

Blockage in the conduction system can cause a slight or severe delay in the electrical impulses propagating through the atrioventricular node 122, causing inadequate ventricular relations and filling. In situations where the blockage in the ventricles (e.g., the right and left bundle branches 126, 128), the right and/or left ventricles 108, 112 can only be excited through slow muscle tissue conduction. As a result, the muscular walls of the affected ventricle (108 and/or 112) do not contract synchronously (e.g., asynchronous contraction), thereby, reducing the overall effectiveness of the heart 100 to pump oxygen-rich blood throughout the body. For example, asynchronous contraction of the left ventricular muscles can degrade the global contractility (e.g., the pumping power) of the left ventricle 112 which can be measured by the peak ventricular pressure change during systole (denoted as "LV+ dp/dt"). A decrease in LV+dp/dt corresponds to a worsened pumping efficiency.

Similarly, heart valve disorders (e.g., valve regurgitation or valve stenosis) can interfere with the heart's 100 ability to pump blood, thereby, reducing stroke volume (i.e., aortic pulse pressure) and/or cardiac output.

Various medical procedures have been developed to address these and other heart disorders. In particular, cardiac resynchronization therapy ("CRT") can be used to improve the conduction pattern and sequence of the heart. CRT involves the use of an artificial electrical stimulator that is surgically implanted within the patient's body. Leads from the stimulator can be affixed at a desired location within the heart to effectuate synchronous atrial and/or ventricular contractions. Typically, the location of the leads (e.g., stimulation site) is selected based upon the severity and/or location of the blockage. Electrical stimulation signals can be delivered to resynchronize the heart, thereby, improving cardiac performance.

Despite these advantages, several shortcomings exist that limit the usefulness of CRT. For example, results from many clinical studies have shown that hemodynamic response to CRT typically varies from patient to patient, ranging from very positive (e.g., improvement) to substantially negative (e.g., deterioration). Additionally, hemodynamic response can also vary based upon the stimulation site used to apply CRT. Thus, in order to predict acute hemodynamic benefit from CRT, the patient typically must be screened prior to receiving the therapy and the actual stimulation site used to apply CRT should be validated for each patient. Existing methods that predict acute hemodynamic response to CRT are, therefore, patient specific. Furthermore, while some existing techniques and/or procedures can predict whether a specific patient will derive an acute hemodynamic benefit from CRT, they are unable to determine or validate that a specific stimulation site will produce a positive hemodynamic response from CRT.

SUMMARY

Embodiments of the present invention provide methods and systems that detect whether a given stimulation site is a responder to CRT. The methods and systems involve making measurements with at least one electrode implanted within the patient's heart. An implanted heart stimulation device, external device programmer, or other device may then determine from the measurements whether the stimulation site is a responder site. An atrioventricular delay to be provided by the stimulation device to provide CRT to the patient can then be set to an appropriate amount based on the status of the stimulation site as a responder or non-responder.

Acute response to cardiac resynchronization therapy may be predicted for a given stimulation site of a patient by inserting a lead to the heart of the patient such that an electrode of the lead is positioned at the stimulation site. A first deflection of an intrinsic ventricular depolarization is then detected, followed by detection of a maximum deflection of the intrinsic ventricular depolarization at the electrode. An interval of time between the first deflection and the maximum deflection is compared to a threshold to determine whether the stimulation site is a responder site.

One system for predicting acute response to cardiac resynchronization therapy at a stimulation site of a patient includes a lead having an electrode placed at the stimulation site that detects an intrinsic ventricular depolarization. A surface electrocardiograph machine also detects the intrinsic ventricular depolarization. A processing device finds an interval of time between a first deflection of the intrinsic ventricular depolarization as detected by the surface electrocardiograph machine and a maximum deflection of the intrinsic ventricular depolarization as detected by the electrode of the lead. The processing device compares the interval to a threshold to determine whether the stimulation site is a responder.

Another system for predicting acute response to cardiac resynchronization therapy at a stimulation site of a patient includes a lead having an electrode placed at the stimulation site that detects an intrinsic ventricular depolarization. A processing device finds an interval of time between the first deflection and the maximum deflection of the intrinsic ventricular depolarization as detected by the electrode and compares the interval to a threshold to determine whether the stimulation site is a responder.

DETAILED DESCRIPTION

Figure 1:
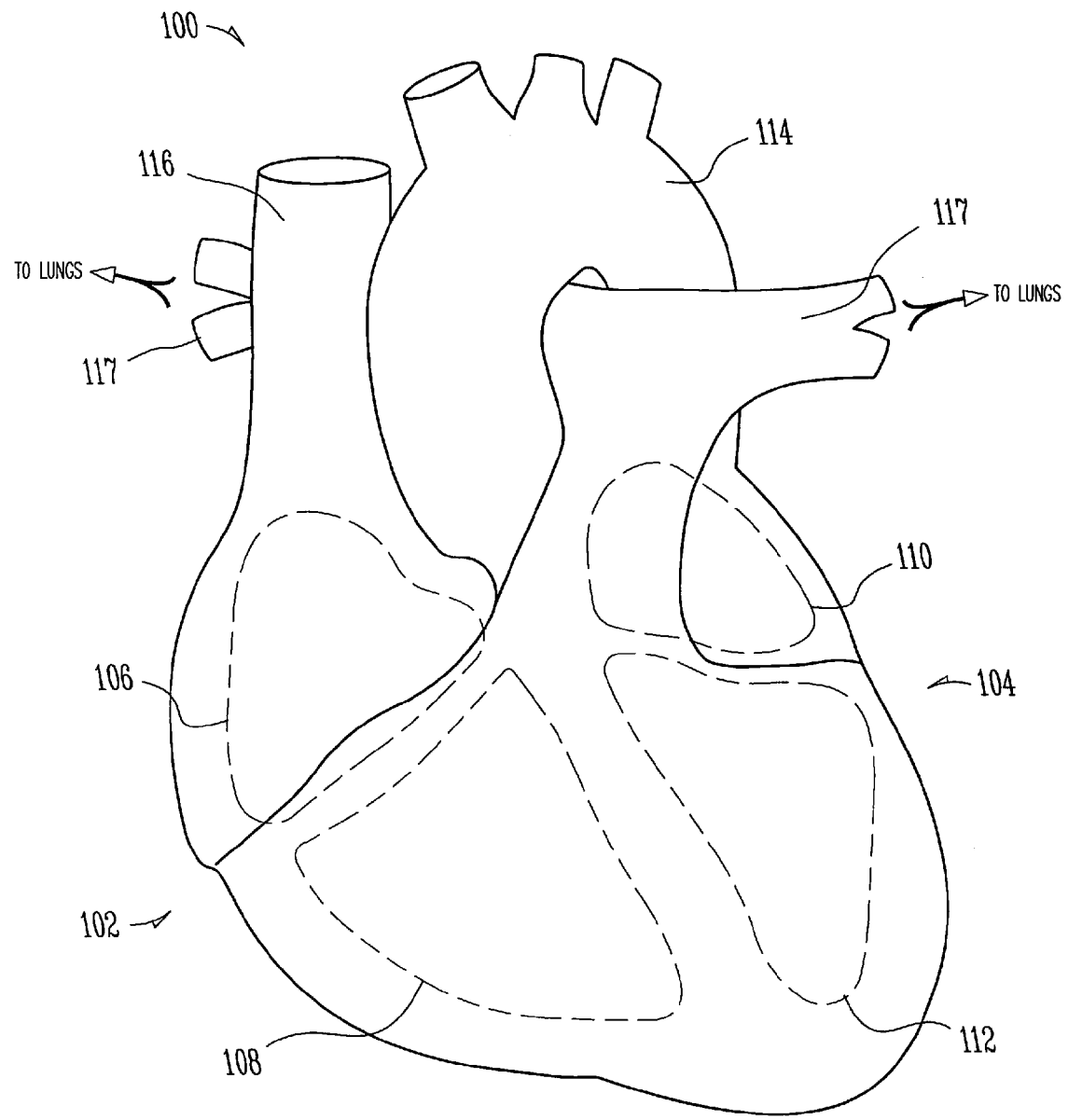
FIG. 1 is a diagram showing the various chambers of the heart.
Figure 2:
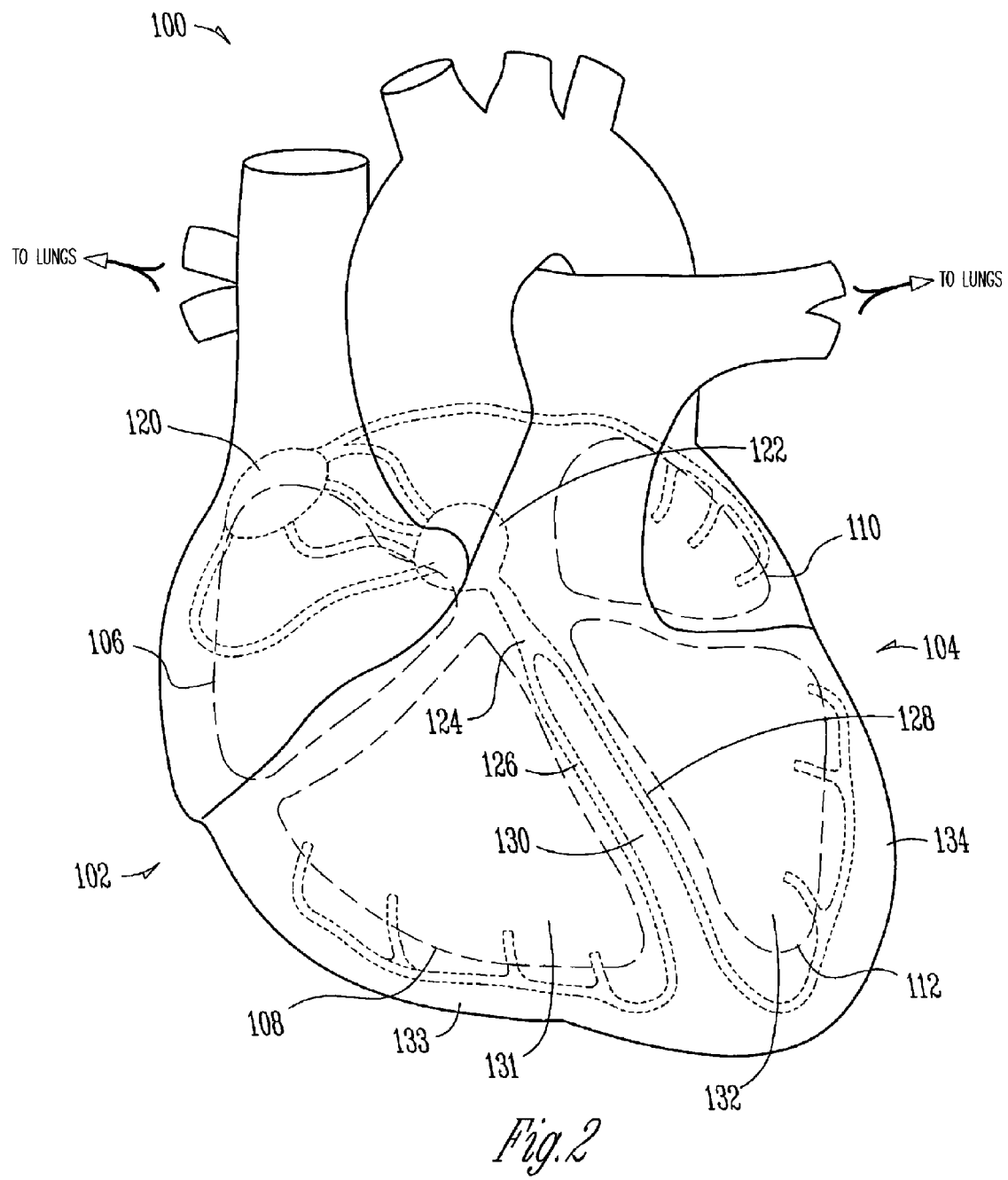
FIG. 2 is a diagram showing the various chambers and the electrical conduction system of the heart.

Various embodiments of the present invention will be described in detail with reference to the drawings, wherein like reference numerals represent like parts and assemblies throughout the several views. Reference to various embodiments does not limit the scope of the present invention, which is limited only by the scope of the claims attached hereto.

The following discussion is intended to provide a brief, general description of a suitable method for predicting whether a stimulation site is a positive responder to cardiac resynchronization therapy ("CRT"). As will be described in greater detail below, the method of the present disclosure predicts a stimulation site's response to CRT by measuring an interval that starts from a first deflection that represents the far field reflexion of the ventricular activation somewhere in the ventricles. The interval continues to a maximum deflection of the same intrinsic ventricular depolarization that represents the near field reflexion of the local activation of the tissue near an electrode, detected at the stimulation site where the response to CRT is being evaluated. The interval is then compared against a threshold, and if the interval is larger than the threshold the site is defined as a positive responder to CRT. If the interval is not larger than the threshold, then the site is defined as a non-responder site.

As will become apparent from the discussion below in connection with the various drawings, the first deflection of ventricular depolarization may be measured in several different ways. For example, an onset of the depolarization may be found through processing of an intracardiac electrogram signal in the window that occurs before the beginning of the large peak that corresponds to the near field ventricular activation for that electrode. As another example, the onset may be found by processing of a signal measured by at least one surface electrode to detect the beginning of the integrated far field activation such as through an ensemble averaging technique similar to that described in U.S. Pat. No. 5,235,976, which may also be applied where intracardiac electrograms are used to find the onset. However, those of ordinary skill in the art will readily appreciate that the method of the present disclosure can be implemented using any suitable first deflection reference besides a representative onset value taken from a surface electrocardiogram or an intracardiac electrogram.

In a preferred embodiment, the method of the present disclosure predicts whether a given stimulation site of a patient will respond to CRT by evaluating the interval from a first deflection to a maximum deflection of depolarization of a ventricle to receive the CRT therapy where at least the maximum deflection is detected by an electrode placed at the stimulation site. The first deflection of ventricular depolarization of the ventricle 108, 112 can be evaluated from intracardiac or surface electrode signals. An electrogram is generally a graphical depiction of the electrical depolarization or excitement of the heart 100 (FIG. 1) that is measured by one or more electrodes placed on or within the heart 100, such as within the right or left ventricles, or alternatively placed on the surface of the patient's body.

Figure 3:
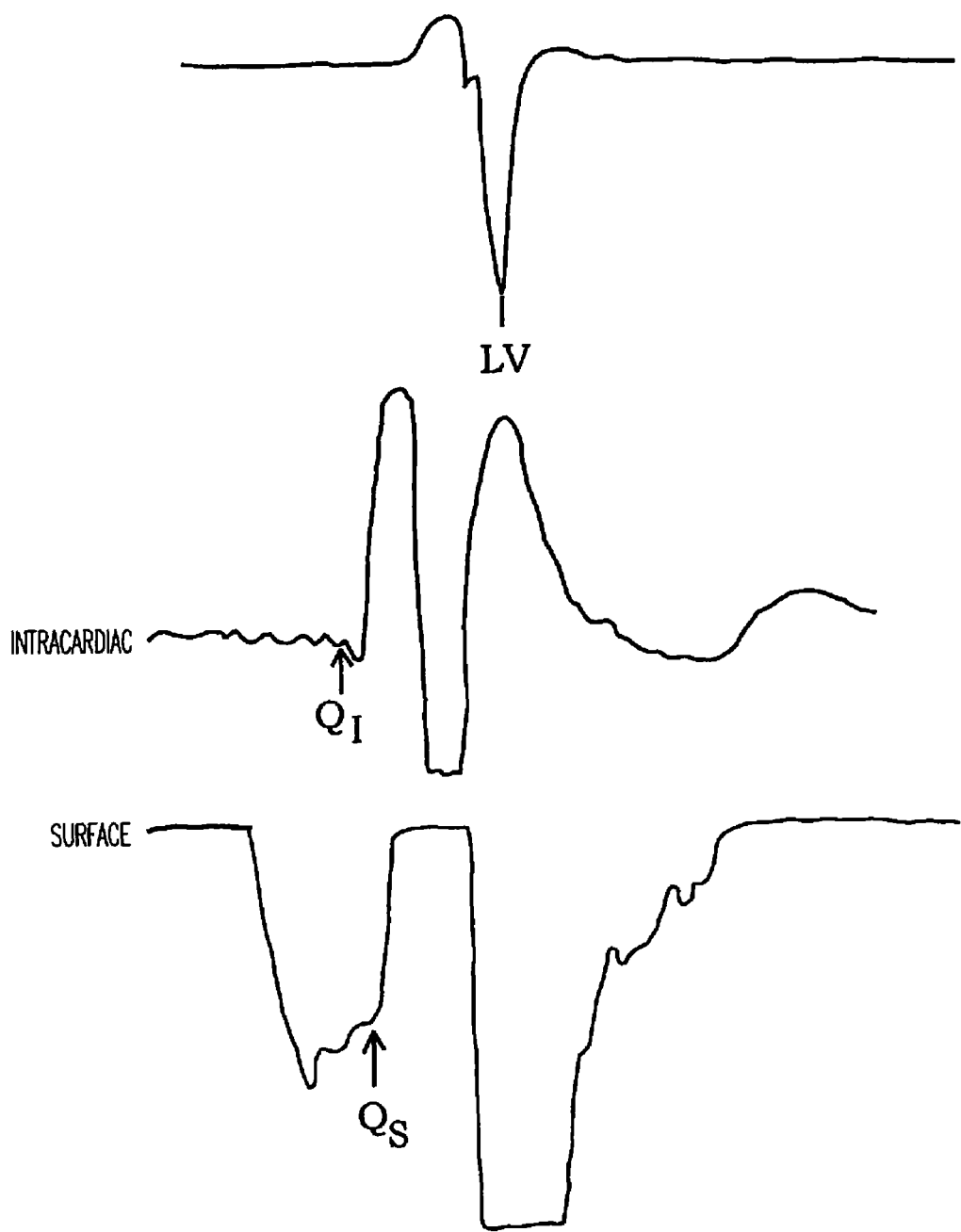
FIG. 3 is a graph showing ventricular depolarization as a function of time and relating the ventricular depolarization as measured by a surface electrocardiograph and as measured by an intracardiac electrogram.

An exemplary pair of electrograms for an intrinsic systolic cycle is shown in FIG. 3 where one electrogram is an intracardiac electrogram and the other is a surface electrogram. Each portion of an electrogram is typically given an alphabetic designation corresponding to a pre-determined period of electrical depolarization or excitement. For example, the portion of an electrogram that represents atrial depolarization is commonly referred to as the P-wave (not shown). Similarly, the portion of the electrogram that represents ventricular depolarization is commonly referred to as the QRS complex comprising a Q-wave, an R-wave, and an S-wave. Moreover, the portion of the electrogram that represents ventricular recovery or repolarization is commonly referred to as the T-wave (not shown).

As shown in FIG. 3, one graph illustrates a maximum deflection peak representing the reflexion on the local electrode of the near field (near the electrode) ventricular activation of the left ventricle labeled LV. Also, shown in FIG. 3 for the intracardiac electrogram is the first deflection labeled QI corresponding to the onset representing the reflexion on the local electrode of the start of the far field ventricular electrical activation. The graph for the surface electrode in FIG. 3 shows the onset of the first deflection of ventricular depolarization that is labeled $Q_s$. As shown in FIG. 3, the intracardiac graph, the surface graph for the onset, and the maximum deflection graph are based upon a different time axes so that detail of each of the different waveforms can be appreciated. It should be noted with reference to FIG. 3 that in practice, QI occurs slightly sooner, typically 20 milliseconds sooner, than QS.

Figure 4:
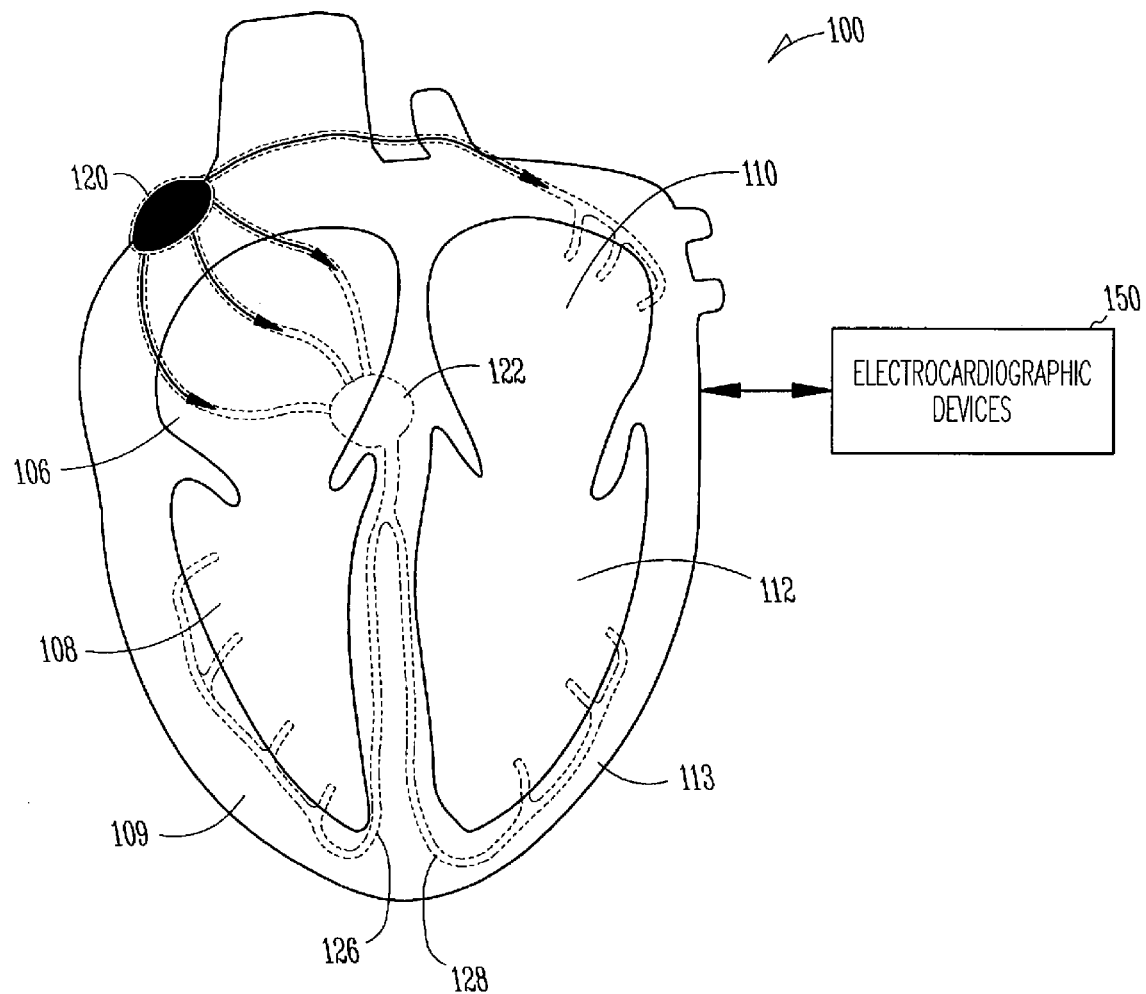
FIGS. 4-6 are diagrams illustrating a heart and the electrical conduction system advancing through a normal cardiac cycle.
Figure 5:
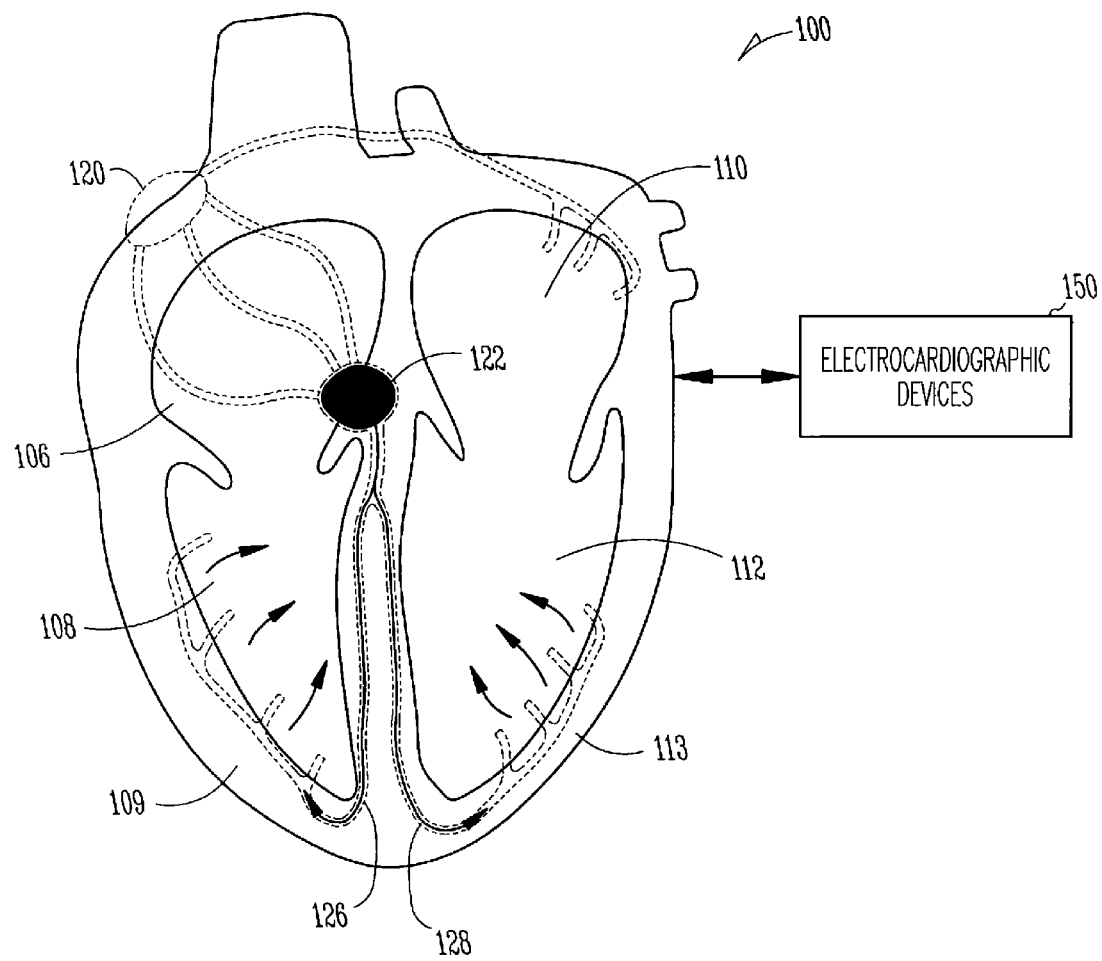
Figure 6:
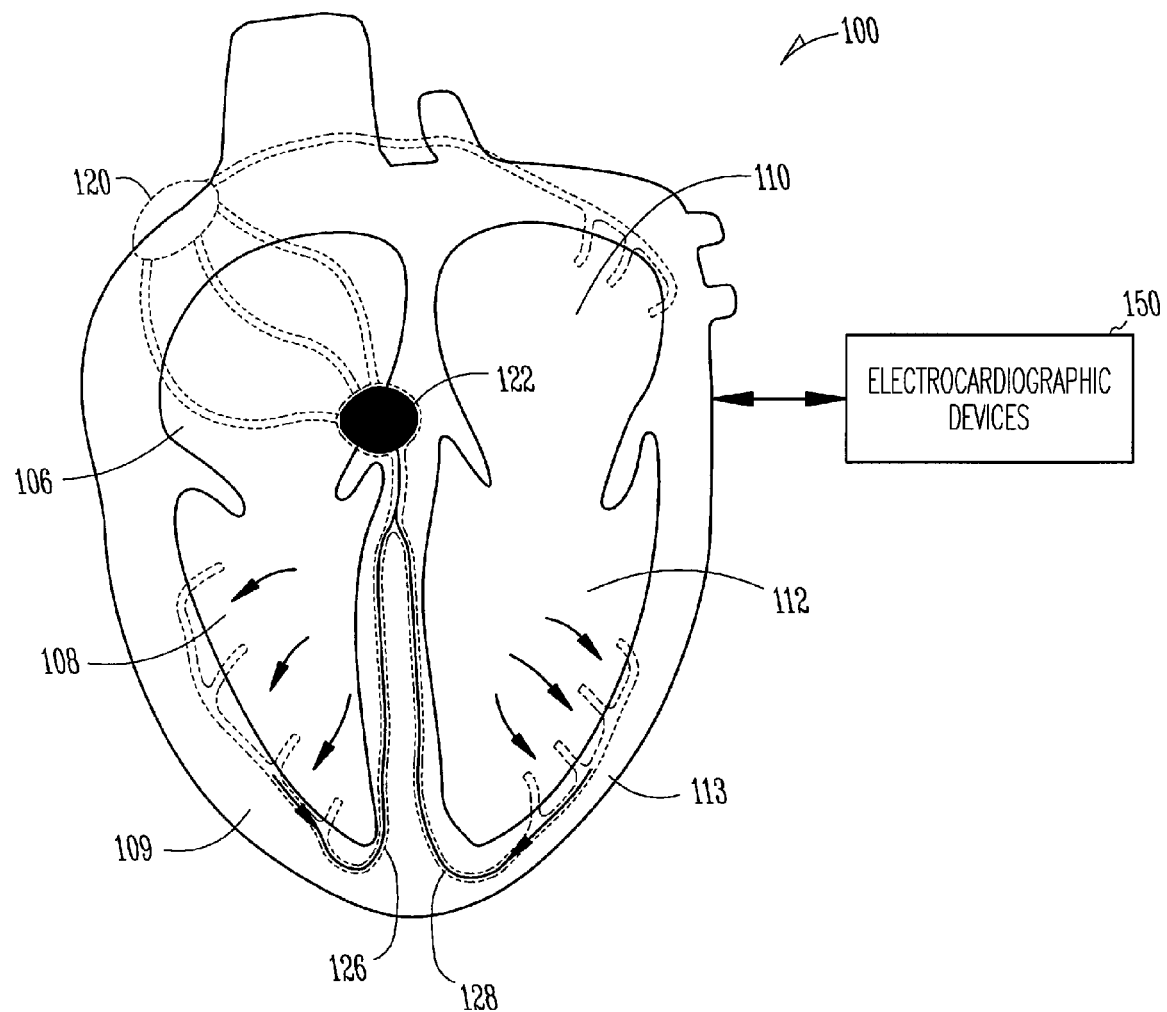

Each period of electrical depolarization or excitement represented on the electrogram corresponds to a period of muscular activation within the heart 100 (FIG. 1). FIGS. 4-6 are schematic illustrations depicting the various periods of muscular activation within the heart 100. As shown in FIGS. 4-6, the electrogram data can be monitored using any suitable electrocardiographic device 150, such as a surface electrocardiograph and/or an implantable heart stimulation device (i.e. CRT device) that is connected to leads located on or within the heart 100 or through a device that combines information from at least one intracardiac electrode and at least one surface electrode. It will be appreciated by one of ordinary skill in the art that many combinations of electrodes can be used to derive an electrogram where the start of the ventricular activation can be detected as a far field signal.

FIG. 4 is a schematic illustration showing the period of atrial activation in response to electrical impulses initiated at the sinoatrial node 120 (corresponding to the P-wave portion as discussed above). After electrical impulses spread from the sinoatrial node 120, the muscle tissues of the right and left atriums 106, 110 contract to pump blood into the right and left ventricles 108, 112, respectively.

FIG. 5 is a schematic illustration showing the period of a ventricular depolarization in response to electrical impulses initiated at the atrioventricular node 122 that spread through the ventricles 108, 112 (corresponding to the QRS portion as discussed above). After electrical impulses spread from the atrioventricular node 122, the muscle tissues of the right and left ventricles 108, 112 contract to pump blood to the lungs and throughout the body, respectively.

In this FIG. 5, a coordinated or synchronous activation of both ventricles and the lateral wall is represented. It is very common in patients undergoing cardiac resynchronization therapy (CRT) that the septum and/or the right ventricle activate first with a late latero-posterior wall activation. Embodiments of the present invention allows detection with any electrode the low level far field signal that corresponds to the start of the ventricular activations, and then compares the time of occurrence of that signal with the time at which the near field activation of the electrode is detected near the site of stimulation. To be able to resynchronize this site with the early activate site, this site needs to be activated late with respect to the beginning of the ventricular activation. This allows the comparison of this time difference, between the earliest activation and the activation at the stimulation site with a threshold. The comparison provides for the determination that the site will be a responder site if that time is larger than the therapeutic threshold for CRT to act in a positive manner.

FIG. 6 is a schematic illustration showing ventricular recovery or repolarization (corresponding to the T-wave portion as discussed above). During ventricular repolarization, the membrane potential of the muscle cells reverse polarity and return to their resting state, thereby, causing the ventricles to relax in a heart without asynchrony.

An electrogram of a patient's heart can be used to assess cardiac performance by validating the existence of cardiac abnormalities, such as, arrhythmias evinced by an abnormally fast heart rate (e.g., tachycardia), an abnormally slow heart rate (e.g., bradycardia), or a normal rate but the depolarization is abnormally propagated (e.g., ectopic, or conduction system defect). The existence of an arrhythmia typically indicates that the heart's rhythm initiation and/or conduction system is functioning abnormally. CRT can be used, among other applications, to treat abnormal electrical conduction. In particular, CRT can be used to deliver electrical stimulation to portions of the heart 100 (FIG. 1) to resynchronize the heart's activation, thereby, improving the efficiency of atrial and ventricular contractions necessary to circulate blood throughout the body. The amount of benefit derived from CRT, however, typically varies depending upon the severity of the abnormality of the heart's conduction system. Therefore, prior to treating a patient using CRT, it is preferable to evaluate whether the heart's 100 (FIG. 1) conduction system is normal or abnormal.

This may be done by using the duration of the surface QRS. Patients with a QRS duration of more than 120-130 ms are considered to have a sufficiently abnormal conduction to benefit from CRT. But once a patient with an abnormal conduction system is found, another problem that needs to be solved is to determine whether the chosen stimulation site is good enough to realize the benefits of CRT. For this site to be effective it needs to be located in a late activate region, henceforth able to resynchronize the ventricles through electrical stimulation.

To determine if a site is a responder site, both the heart's ventricular conduction system and the chosen site must be assessed. These can be assessed through analysis of the interval (QI-LV or QS-LV) from the first deflection (QI or QS) to the maximum deflection (LV) at the stimulation site of the ventricular depolarization. Identification of stimulation sites that may have a positive response to CRT can be performed using the interval above where at least the maximum deflection point (LV) is measured from an intracardiac electrogram. For example, if the interval (QI-LV or QS-LV) is greater than a given threshold, then the stimulation site may be considered a responder to CRT, and the CRT device for that patient may be configured appropriately.

Once a stimulation site has been deemed a responder or non-responder, the CRT device can be configured to stimulate the heart to produce an atrioventricular delay of a duration appropriate for the type of site as is discussed below. The atrioventricular delay of an implantable device is generally considered to be the length of time between an atrial sensed (or stimulated) event and the delivery of a ventricular output pulse. For a responder site, the atrioventricular delay is set to substantially less than the intrinsic, or naturally occurring atrioventricular interval, generally to about one-half of the intrinsic interval. This delay may be measured from sensed intrinsic atrial activity to the first ventricular activation in the case of no atrial pacing or may be measured from the atrial pacing spike to the first ventricular activation in the case of atrial pacing. For a non-responder site, the atrioventricular delay is set to approximately the intrinsic atrioventricular interval, such as 70% of the intrinsic interval, but at least about 50 milliseconds less than the intrinsic interval. This setting is somewhat less than the intrinsic interval so that the intrinsic activity does not occur prior to and interfere with the stimulation from the device. As discussed for responders above, this delay may be measured from the sensed intrinsic atrial activity to the first ventricular activation for no atrial pacing or measured from the atrial pacing spike to the first ventricular activation in the case of atrial pacing. One with ordinary skill in the art will recognize that other atrioventricular delay settings for responder sites and non-responder sites are possible as well.

Figure 7:
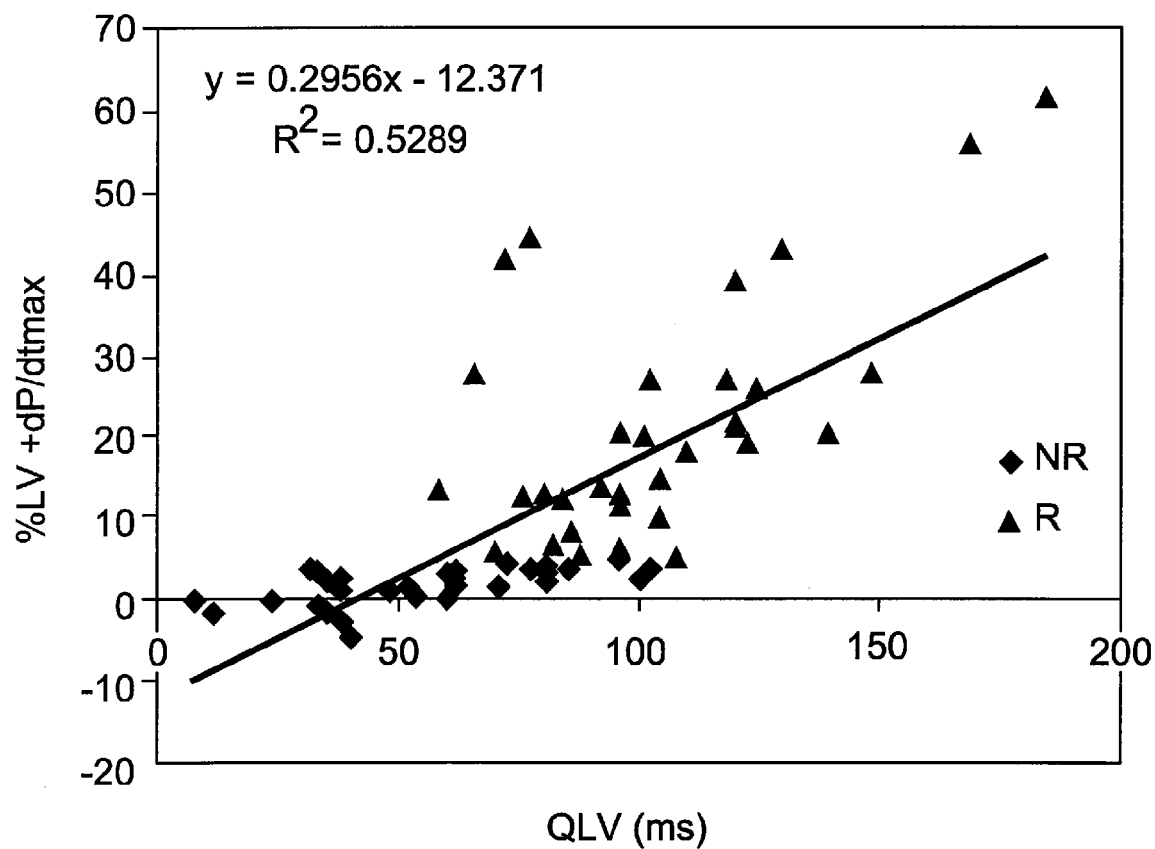
FIG. 7 is a graph illustrating mean percentage change in left ventricular pressure (LV+dp/dt) resulting from application of CRT plotted against the interval of first deflection to maximum deflection of intrinsic ventricular depolarization for responder and non-responder sites.

FIG. 7 shows a graph of the mean percent change in peak rate of increase of left ventricle pressure "LV dp/dt" after application of CRT over multiple atrioventricular delays for a group of patients consisting of both responder stimulation sites and non-responder stimulation sites. Responder sites may be defined as those sites where when stimulated through CRT, the patient received an increase in rate of increase of peak left ventricle pressure of more than 5%. From the graph, one can see that a relationship exists between the intrinsic depolarization interval (QS-LV) and the increase in peak rate of increase of left ventricle pressure due to CRT. For those stimulation sites having a relatively long first deflection to maximum deflection interval (QS-LV), CRT caused a relatively large increase in peak rate of increase of left ventricle pressure. For those having a relatively short QS-LV interval, CRT caused a relatively small increase or in some instances a decrease in peak rate of increase of left ventricle pressure. The QS-LV data of FIG. 7 was based on the QS onset value discussed above and that may be found by the process disclosed in commonly owned co-pending U.S. patent application Ser. No. 10/004,695 entitled Apparatus and Methods for Ventricular Pacing Triggered by Detection of Early Ventricular Excitation that applies to an intraventricular unipolar electrogram. An intraventricular unipolar electrogram is one where the potential difference created by the heart's activity is measured from a surface electrode, in our case a patch on the patients chest, to the intraventricular electrode.

A linear regression of the test cases shows that the correlation of percent change in peak left ventricle pressure to QS-LV is defined by the equation $y=0.2956x-12.371$, with a coefficient of determination $R^2=0.5289$. A threshold of 80 milliseconds appears to be a suitable value for distinguishing responder sites from non-responder sites, although one skilled in the art will recognize that other threshold values may be applicable as well. This threshold provides a sensitivity of 81%, which represents the probability of correct classification of stimulation sites as responders, and also provides a specificity of 83%, which is the probability of correct classification of stimulation sites as non-responders. Because QI is typically sensed 20 milliseconds earlier than QS, the threshold of 80 milliseconds for QS-LV may be extended to 100 milliseconds for the interval QI-LV, when intracardiac sensing of the onset is used.

Figure 8:
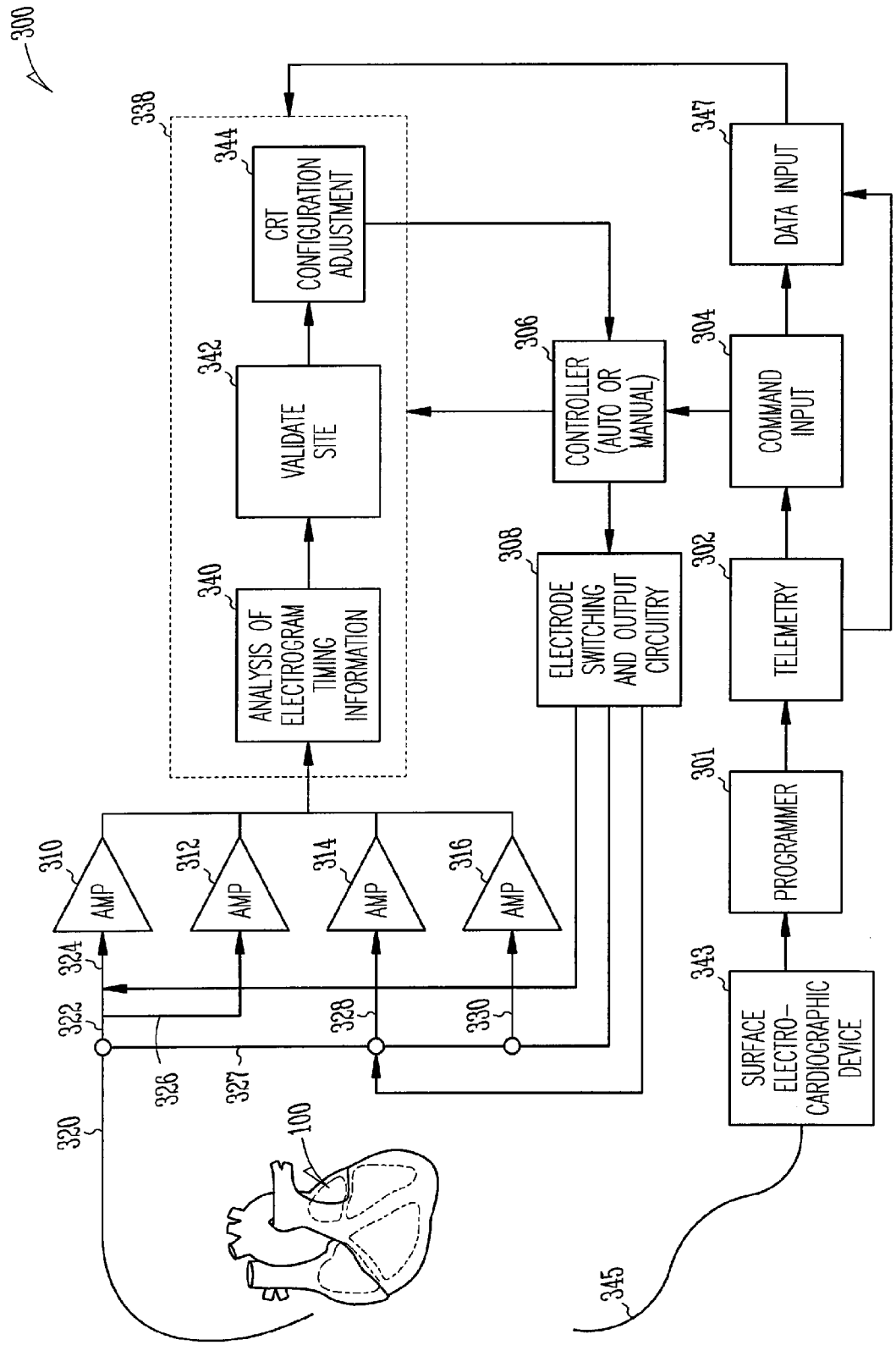
FIG. 8 illustrates one possible embodiment of a system that can be used to detect whether a stimulation site is a responder to CRT by utilizing a surface electrocardiogram to detect the onset of ventricular depolarization.

One possible embodiment of a CRT system 300 that can be used to implement the methods for determining whether a stimulation site is a responder site is illustrated in FIG. 8. As shown in FIG. 8, the CRT system 300 generally comprises a programming device 301 that can be used to program the CRT device and control its diverse parameters (i.e. HR, AV delay, PVARP, etc.). In one possible embodiment, the heart 100 is connected to various leads 320 having electrodes (not shown) and terminal pins (not shown) that can connect the heart 100 to the CRT system 300. The various leads 320 connecting the heart 100 to the CRT system 300 will be described in greater detail below.

The programmer 301 can regulate the stimulation pulses delivered to the heart 100 using, for example, a telemetry module 302 to communicate instructions to an implantable CRT device applying the stimulation pulses. In one possible embodiment, the telemetry module 302 is unidirectional (e.g., capable of allowing the programmer 301 to receive data). However, in an alternative embodiment, the telemetry module 302 is bi-directional (e.g., capable of allowing the programmer 301 to receive and/or send data). The command input module 304 of an implantable CRT device is configured to interpret the data received from the programmer 301 such that the stimulation pulses can be accurately distributed according to predetermined criteria, such as, the specific requirements of the patient being treated.

A controller 306 of the implantable CRT device can be used to control the specific instructions regarding the stimulation pulses delivered to the heart 100. In one possible embodiment, the controller 306 can be controlled manually. In an alternative embodiment, however, the controller 306 can be controlled automatically using, for example, feedback received from an intrinsic signal analyzer 338 of the implantable CRT device. The instructions from the controller 306 are received by an electrode switching and output circuitry module 308 of the implantable CRT device that delivers the stimulation pulses to the appropriate lead 320 within the heart 100.

As discussed above, the heart 100 is connected to the CRT system 300 using various leads 320. The various leads 320 are preferably configured to carry the CRT stimuli from the implantable CRT device to the heart 100. Moreover, the various leads 320 can likewise operate in a demand mode, thereby, relaying intrinsic cardiac signals from the heart's 100 electrical conduction system back to one or more sense amplifiers 310, 312, 314, 316 of the implantable CRT device. In one possible embodiment, the various leads 320 comprise separate and distinct leads connecting the CRT system 300 to different portions of the heart 100. In particular, the various leads 320 can comprise a lead 322 connected to the right-side portion or pump 102 (FIG. 1) of the heart 100, including, for example, a right atrium lead 324 configured to operate with a right atrium amplifier 310 and a right ventricle lead 326 configured to operate with a right ventricle amplifier 312. Similarly, the various leads 320 can comprise a lead 327 connected to the left-side portion or pump 104 (FIG. 1) of the heart 100, including, for example, a first left ventricle lead 328 configured to operate with a first left ventricle amplifier 314 and a second left ventricle lead 330 configured to operate with a second left ventricle amplifier 316.

As discussed above, the various leads 320 connected to the heart 100 can relay intrinsic cardiac signals from the heart's 100 electrical conduction system back to the one or more sense amplifiers 310, 312, 314, 316. The intrinsic cardiac signals amplified by the sense amplifiers 310, 312, 314, 316 can then be processed by a signal analyzer 338 incorporated in whole or in part by an implantable heart stimulation device (i.e., CRT device) receiving the surface electrocardiogram data through telemetry 302, or alternatively by the device programmer 301 that receives the intracardiac electrogram signal through telemetry 302. One of ordinary skill in the art will appreciate that the signal analyzer 338 could be either located in the CRT device or in the programmer unit or in both depending upon the architectural requirements of the system and on the degree of autonomy required of the CRT device once disconnected from the programmer. In the embodiment described in FIGS. 8 and 9 the signal analyzer 338 is located in the CRT device.

Additionally, the CRT system includes an electrocardiographic (ECG) device 343 that includes leads 345 that provide electrodes on the surface of the patient's body to detect cardiac signals. The cardiac signals include the ventricular depolarization signal shown in FIG. 3. The ECG device 343 relays this signal to the device programmer 301 for subsequent relay to the signal processing unit 338 through telemetry and data input unit 347. Alternatively, the ECG device 343 provides a timing of the first deflection to the programmer 301 rather than relying on the programmer 301 or signal analyzer 338 to determine from the cardiac signal when the first deflection occurred. The electrocardiograph is a set of amplifiers and switches with connectors for the electrodes located in the surface of the body of the patient, and this set of components could be integrated into the programmer and be an indistinguishable part of the programmer system.

The intrinsic signal analyzer 338 generally can comprise a detection module 340 that is configured to analyze the intracardiac electrogram and/or surface electrocardiogram information to detect the first deflection (QS) and maximum deflection of local ventricular depolarization (LV) values discussed above with reference to FIG. 3. In the embodiment described by FIG. 8 the detection module 340 is equipped to analyze the surface electrocardiogram information or to receive the QS times directly from the programmer or electrocardiographic unit. The QS and LV values are then processed by the processing module 342 to detect a responder or non-responder site and the result is implemented by the configuration module 344 by setting the atrioventricular delay as appropriate for the particular type of site by interacting with the controller 306. The processing performed by processing module 342 is discussed in more detail below with reference to FIG. 10.

Figure 9:
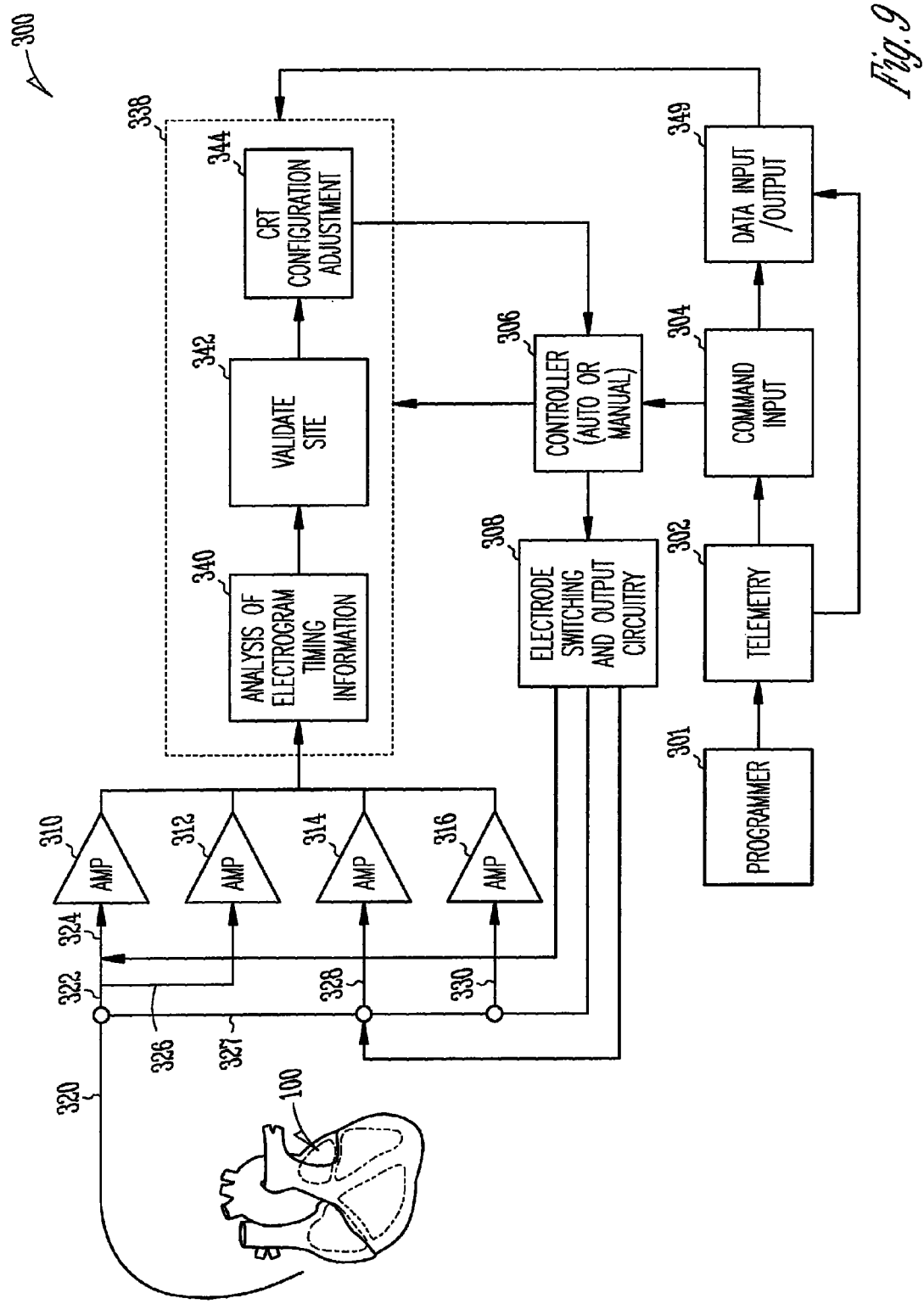
FIG. 9 illustrates another possible embodiment of a system that can be used to detect whether a stimulation site is a responder to CRT by utilizing intracardiac sensing to detect the onset of ventricular depolarization.

Another possible embodiment of a CRT system 300 that can be used to implement the methods for determining whether a patient is a responder is illustrated in FIG. 9 and comprises many of the same components as the embodiment of FIG. 8 which function in the same manner as previously discussed, except that no surface electrocardiographic device is utilized in the embodiment of FIG. 9.

As discussed above, the various leads 320 connected to the heart 100 can relay intrinsic cardiac signals from the heart's 100 electrical conduction system back to the one or more sense amplifiers 310, 312, 314, 316. The intrinsic cardiac signals amplified by the sense amplifiers 310, 312, 314, 316 can then be processed by an intrinsic signal analyzer 338 incorporated in whole or in part by the implantable heart stimulation device (i.e., CRT device) or a device programmer 201 that receives intracardiac signals from the implantable CRT device through data input/output module 349 and telemetry 302. The intrinsic signal analyzer 338 generally can comprise a detection module 340 that is configured to analyze the intracardiac electrogram information to detect both the first deflection (QI) and the maximum deflection (LV) of ventricular depolarization. The QI-LV values are then processed by the processing module 342 as discussed below with reference to FIG. 10, and the result is implemented by the configuration module 344 setting the appropriate atrioventricular delay.

The method of the present disclosure can be implemented using a CRT system as shown in FIG. 8 or 9 comprising various devices and/or programmers, including implantable or external CRT devices and/or programmers such as a CRT tachy or brady system. Accordingly, the method of the present disclosure can be implemented as logical operations controlling a suitable CRT device and/or programmer. The logical operations of the present disclosure can be implemented: (1) as a sequence of computer implemented steps running on the CRT device and/or programmer; and (2) as interconnected machine modules within the CRT device and/or programmer. The implementation is a matter of choice dependant on the performance requirements of the CRT device and/or programmer implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

Figure 10:
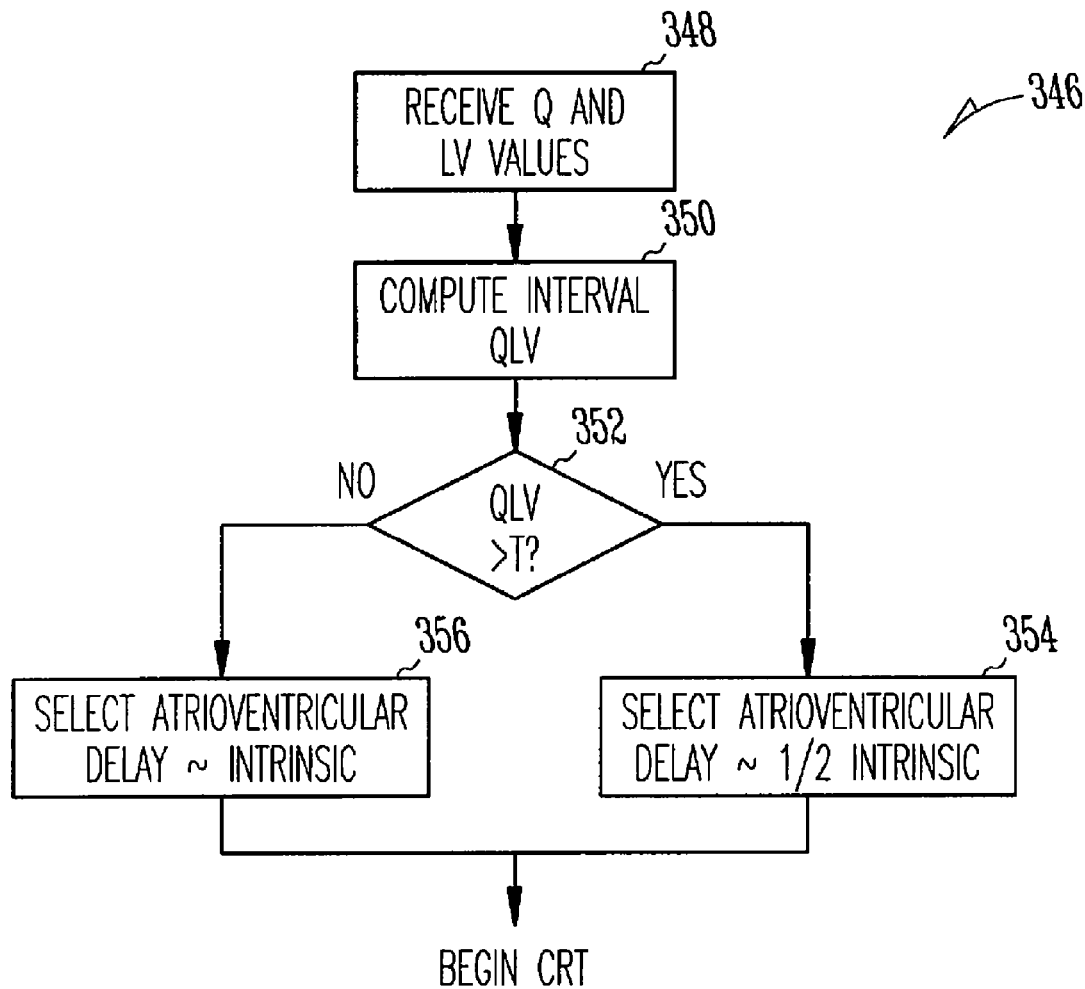
FIG. 10 is an operational flow summarizing the logical operations employed by an exemplary system for detecting whether a patient is a responder to CRT.

FIG. 10 shows an exemplary embodiment 346 of the logical operations of the processing module 342. The process begins by the processing module 342 receiving the QI or QS and LV time values from the signals measured by detection module 340 and/or ECG device 343 at receive operation 348. At interval operation 350, the processing module 342 computes the time interval between the QI or QS and LV values. At query operation 352, the processing module 342 compares the QI-LV or QS-LV interval to the threshold, such as 100 milliseconds for QI-LV and 80 milliseconds for QS-LV.

If the processing module 342 determines that QI-LV or QS-LV is greater than the threshold, then the processing module 342 selects an atrioventricular delay that is about one-half of the intrinsic atrioventricular delay at delay operation 354. If the processing module 342 determines that QI-LV or QS-LV is less than or equal to the threshold, then the processing module 342 selects an atrioventricular delay that is approximately equal to the intrinsic atrioventricular delay at delay operation 356. As discussed above, it is desirable at delay operation 356 to set the atrioventricular delay to the intrinsic atrioventricular delay value less a small delay factor such that the atrioventricular delay is around 70% of the intrinsic interval but is always at least 50 milliseconds less than the intrinsic interval. The configuration module 344 then implements the atrioventricular delay selected by processing module 342 when applying CRT or other pacing therapy to the patient.

While the invention has been particularly shown and described with reference to preferred embodiments thereof, it will be understood by those skilled in the art that various other changes in the form and details may be made therein without departing from the spirit and scope of the invention.

What is claimed is:

1. A system, comprising:
   a device programmer having sensing circuitry connected to a first electrode adapted for placement on the body of a patient and adapted for generating a surface electrocardiogram;
   an implantable device in communication with the device programmer and having sensing circuitry connectable to a second electrode adapted for placement at a myocardial stimulation site and adapted for generating an electrogram;
   wherein the device programmer is programmed to measure a time interval between a deflection of the surface electrocardiogram generated by the first electrode and a deflection of the electrogram generated by the second electrode during an intrinsic systolic cycle;
   wherein the device programmer is further programmed to compare the measured time interval to a threshold and to compute an atrioventricular delay for delivering pacing pulses to the myocardial stimulation site in accordance with whether the interval is less than or greater than the threshold.

2. The system of claim 1 wherein the device programmer is programmed to compute a shorter atrioventricular delay when the interval is greater than the threshold and a longer atrioventricular delay when the interval is less than the threshold.

3. The system of claim 1 wherein the device programmer is programmed to compute the atrioventricular delay as substantially less than an intrinsic atrioventricular delay of the patient when the interval is greater than the threshold.

4. The system of claim 1 wherein the device programmer is programmed to compute the atrioventricular delay as a value no greater than 50% of an intrinsic atrioventricular delay of the patient when the interval is greater than the threshold.

5. The system of claim 1 wherein the device programmer is programmed to compute the atrioventricular delay as a value no less than 70% of an intrinsic atrioventricular delay of the patient when the interval is less than the threshold.

6. The system of claim 1 wherein the threshold is approximately 80 milliseconds.

7. The system of claim 1 wherein the device programmer is programmed to measure the time interval as the time interval between a first deflection of the surface electrocardiogram generated by the first electrode and a maximum deflection of the electrogram generated by the second electrode.

8. The system of claim 1 wherein the device programmer is programmed to communicate the computed atrioventricular delay to the implantable device.

* * * * *